United States Patent
Murphy et al.

(10) Patent No.: US 8,227,423 B2
(45) Date of Patent: Jul. 24, 2012

(54) **ANTIBACTERIAL PEPTIDE WITH ACTIVITY AGAINST *B. ANTHRACIS***

(75) Inventors: John Murphy, Boston, MA (US); Robert J. Harrison, Medfield, MA (US)

(73) Assignee: Boston Medical Center Corporation, Boston, MA (US)

( * ) Notice: Subject to any disclaimer, the term of this patent is extended or adjusted under 35 U.S.C. 154(b) by 1211 days.

(21) Appl. No.: 11/662,555

(22) PCT Filed: Sep. 20, 2005

(86) PCT No.: PCT/US2005/033376
§ 371 (c)(1),
(2), (4) Date: Jan. 31, 2008

(87) PCT Pub. No.: WO2006/034134
PCT Pub. Date: Mar. 30, 2006

(65) Prior Publication Data
US 2008/0249023 A1    Oct. 9, 2008

Related U.S. Application Data

(60) Provisional application No. 60/611,507, filed on Sep. 20, 2004.

(51) Int. Cl.
*A61K 38/10* (2006.01)
*A01N 63/00* (2006.01)

(52) U.S. Cl. .................. 514/21.4; 530/326; 424/93.46; 588/249.5

(58) Field of Classification Search ................ None
See application file for complete search history.

(56) References Cited

U.S. PATENT DOCUMENTS

2002/0051791 A1 * 5/2002 Galloway et al. .......... 424/190.1

FOREIGN PATENT DOCUMENTS

WO    01/35981 A1    5/2001

OTHER PUBLICATIONS

Lockwood, The Biochemical Journal, Feb. 15, 2004, vol. 378, No. Pt 1, pp. 93-103.*

Lockwood, Nathan A., "Acylation of SC4 dodecapeptide increases bactericidal potency against Gram-positive bacteria, including drug-resistant strains." The Biochemical Journal, Feb. 15, 2004, vol. 378, No. Pt 1, pp. 93-103.

* cited by examiner

*Primary Examiner* — Karlheinz R Skowronek
*Assistant Examiner* — Satyanarayana R Gudibande
(74) *Attorney, Agent, or Firm* — Lerner, David, Littenberg, Krumholz & Mentlik, LLP

(57) ABSTRACT

Disclosed is a therapeutic peptide useful in the treatment or prevention of infection caused by Gram-positive bacteria such as *Bacillus anthracis*.

12 Claims, 4 Drawing Sheets

SENSITIVITY OF E. coli DH5α TO PAD-1.17

SENSITIVITY OF E. coli DC2 TO PAD-1.17

FIG. 2A
SENSITIVITY OF B. ANTHRACIS STERNE TO PAD-1.17

FIG. 2B
SENSITIVITY OF B. SUBTILIS TO PAD-1.17

FIG. 3

ACTIVITY OF PAD-1.17 ON B. anthracis STERNE

+PAD1    -PAD1

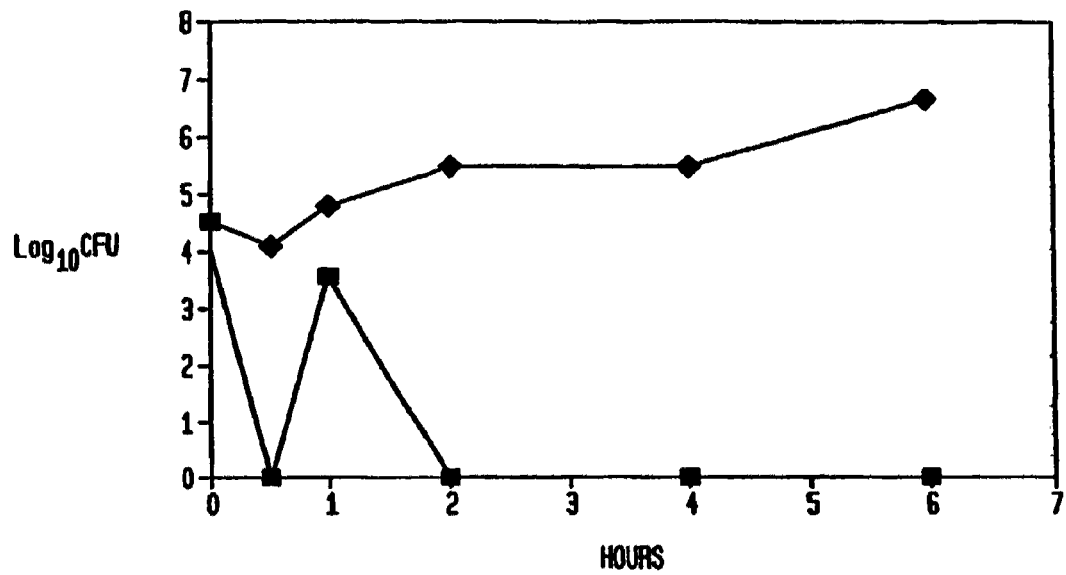
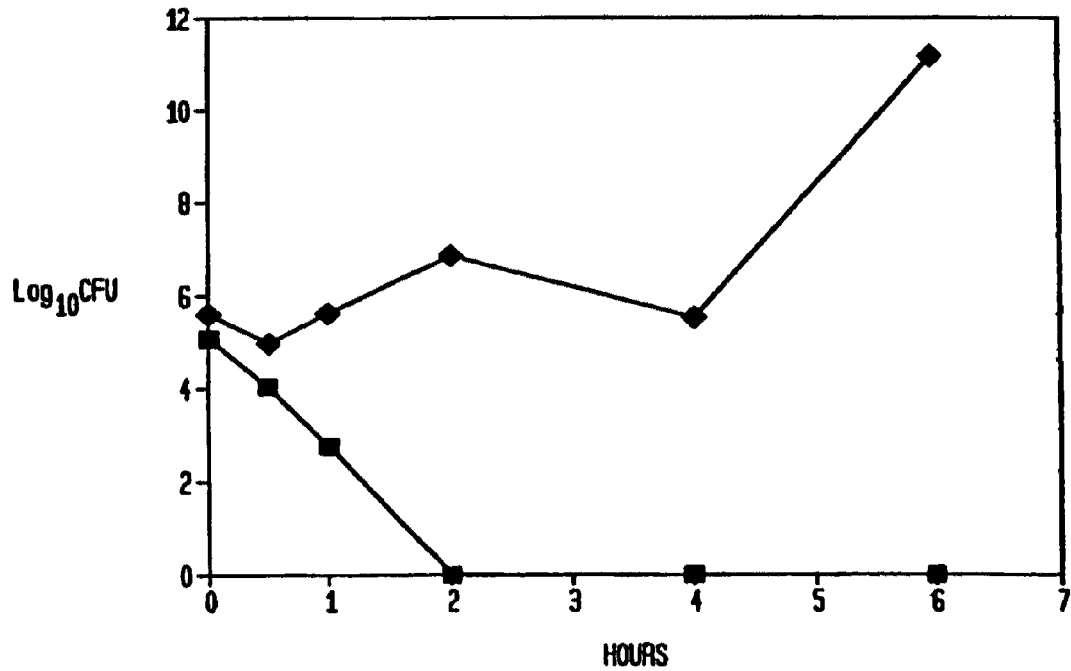

ANTIBACTERIAL PEPTIDE WITH ACTIVITY AGAINST B. ANTHRACIS

GOVERNMENT SUPPORT

Applicants' invention was supported in part by Public Health Service Grant NIH/NIAID AI021628 from the National Institute of Health. Therefore, the government may have certain rights in the invention.

CROSS REFERENCE TO RELATED APPLICATIONS

The present application is a national phase entry under 35 U.S.C. §371 of International Application No. PCT/US2005/033376, filed Sep. 20, 2005, published in English, which claims benefit of U.S. Provisional Patent Application No. 60/611,507, filed Sep. 20, 2004. The disclosures of all of said applications are incorporated by reference herein.

SEQUENCE LISTING

The instant application contains a Sequence Listing which has been submitted via EFS-Web and is hereby incorporated by reference in its entirety. Said ASCII copy, created on Sep. 26, 2011, is named BOSTU 3.3-003 Sequence Listing_ST25.txt and is 791 bytes in size.

BACKGROUND OF THE INVENTION

*Bacillus anthracis* is the etiologic agent responsible for anthrax. The most deadly form of anthrax, as well as the form exploited for use as a biological weapon, is inhalation anthrax, in which spores are inhaled and germinate inside alveolar macrophages in the lung, eventually leading to a systemic infection. Although the mechanism of anthrax intoxication is relatively well understood, virulent *Bacillus anthracis* continues to represent a significant health threat. (See, e.g., "The Anthrax Toxin Complex" by S. H. Leppla, Sourcebook of Bacterial Protein Toxins, p. 277, J. E. Alouf (ed.), Academic Press, London (1991)).

SUMMARY OF THE INVENTION

A first aspect of the present invention is directed to a composition of matter comprising a peptide having (consisting of) the sequence TRKKLFHIFHATIRSR (SEQ ID NO: 1) (subsequently referred to as PAD-1.17).

A second aspect of the present invention is directed to a composition comprising a peptide having the sequence TRKKLFHIFHATIRSR (PAD-1.17) (SEQ ID NO: 1), and a carrier, preferably a pharmaceutically acceptable carrier. The compositions may be used to treat infections caused by Gram-positive bacteria such as *B. anthracis* in humans.

A third aspect of the present invention is directed to a method of treating a infection caused by Gram-positive bacteria in a human comprising administering to the human an effective amount of a peptide having the sequence TRKKLF-HIFHATIRSR (PAD-1.17) (SEQ ID NO: 1).

The peptide of the present invention does not exhibit cationic detergent-like properties at concentrations that have antibacterial activity. As shown in the examples, the peptide of the present invention kills *E. coli, Bacillus subtilis* and *Bacillus anthracis* Sterne, the acapsular form of *Bacillus anthracis*. This peptide has also been shown to effect the destruction of vegetative cells upon emergence from germinating spores.

BRIEF DESCRIPTION OF THE DRAWINGS

FIG. 2A is a line graph depicting the time kill assay of *B. anthracis* Sterne, performed in chelated media, in the presence (squares) or absence (diamonds) of PAD-1.17.

FIG. 2B is a line graph depicting the time kill assay of *B. subtilis* in the presence of 100 μM (X) or 50 μM (triangles) of PAD-1.17, or in the absence (diamonds) of PAD-1.17 or in the presence of 100 μM of protein kinase C substrate inhibitor peptide (PKC 19-31) (squares) having the sequence RFARK-GALRQKNV (SEQ ID NO: 2) having a similar pI and M W Verspohl, E. J. and Wienecke, A., "The role of protein kinase C in the desensitization of rat pancreatic islets to cholinergic stimulation.". J. Endocrinol. 159, 287-295, (1998).

FIG. 3 is a copy of a photograph depicting growth of *B. anthracis* Sterne in the presence or absence of PAD-1.17.

FIG. 4A is a line graph depicting germination of *B. anthracis* Sterne spores in the presence (squares) or absence (diamonds) of PAD-1.17.

FIG. 4B is a line graph depicting germination of *B. subtilis* spores in the presence (squares) or absence (diamonds) of PAD-1.17.

DETAILED DESCRIPTION

Figure 1A:
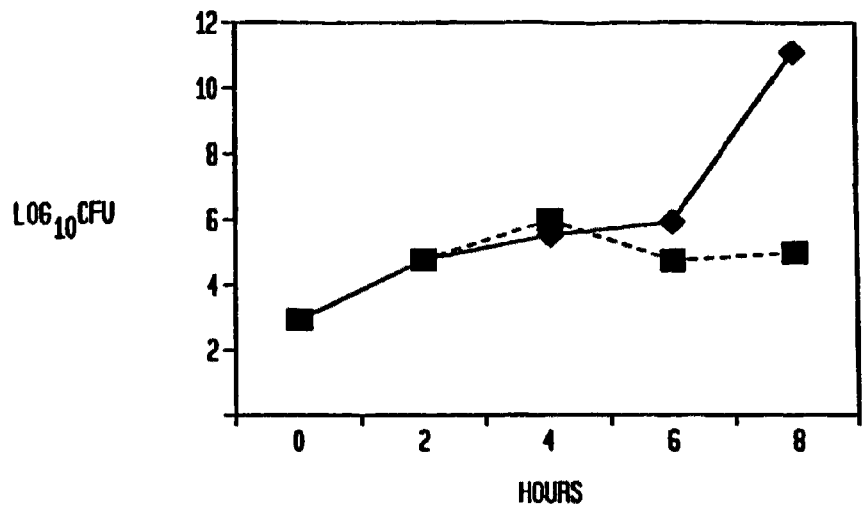
FIG. 1A is a line graph depicting the time kill assay of *E. coli* DH5α in the presence (dashed line) or absence (solid line) of PAD-1.17.

The peptide of the invention may be provided in the form of pharmaceutically acceptable salts. Suitable salts include base salts such as alkali metal salts (e.g., sodium or potassium salts), ammonium salts, and acid addition salts such as hydrochloride and acetate salts.

The peptide of the present invention may be produced using a solid-phase peptide synthesis technique, or in vitro coupled or uncoupled transcription and translation. Synthetic schemes are preferred. The peptide of the invention can be synthesized according to standard methods such as those described in Escobedo, J. A., et al., Mol. Cell. Biol. 11:1125-1132 (1991). In particular, the peptide can be prepared by liquid or solid-phase methodologies including those suitable for large scale production and which are known to those skilled in the art. (Schroeder, et al., "The Peptides", Vol. I, Academic Press 1965, or Bodanszky, et al., "Peptide Synthesis", Interscience Publishers, 1966, or McOmie (ed.) "Protective Group in Organic Chemistry", Plenum Press, 1973, or Barany et al., "The Peptides: Analysis, Synthesis, Biology" 2, Chapter 1, Academic Press, (1980) or Andersson L, Blomberg L, Flegel M, Lepsa L, Nilsson B, Verlander M. (2000); Large-scale synthesis of peptides. Biopolymers. 55(3):227-50)). In the case of solid-phase synthesis, any manual or automatic peptide synthesizer can be used and the peptide can be assembled in a stepwise-manner on a resin support using either Boc or Fmoc strategies.

The peptide may be purified in accordance with standard techniques such as HPLC or reverse-phase HPLC.

The peptide of the present invention may be useful in the treatment of infections caused by Gram-positive bacteria, including Gram-positive, spore-forming bacteria. In some embodiments, the peptide is used to treat infections caused by a species of *Bacillus*, such as *B. cereus* or *B. anthracis* (which causes anthrax). In preferred embodiments, the peptide of the present invention may be used to treat humans presenting with anthrax (e.g., cutaneous or pulmonary). The peptide may also be used to treat humans at risk of contracting anthrax (e.g., a human that has been exposed or suspected to have been exposed, or come into contact with the bacterium). Infections caused by species of *Escherichia* e.g., *E. coli* and *E. faecalis*, may also be amenable to treatment with the peptide of the present invention. Such humans may be treated by formulating the peptide with an appropriate pharmaceutically acceptable carrier or vehicle so as to be administered to the human in the desired fashion.

The peptide of the present invention may be formulated into pharmaceutical preparations for administration via different routes including parenteral e.g., intravenous, and topical (e.g., via creams, salves or iontophoresis).

The peptide may be formulated for parenteral administration by injection, e.g., by bolus injection or continuous infusion. Formulations for injection may be presented in unit dosage form, e.g., in ampoules or in multi-dose containers, with an added preservative. The peptide may be formulated in an appropriate buffer such as phosphate buffered saline (PBS) or other physiologically compatible solutions, which are well suited for I.V. administration. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Formulations for topical application, which would be useful in the treatment of cutaneous anthrax, may include creams and ointments. Administration may also be conduced iontophoretically, whereby the peptide is delivered subcutaneously without an actual injection. See, Boinpally R R, Zhou S L, Devraj G, Anne P K, Poondru S, Jasti B R. (2004) Iontophoresis of lecithin vesicles of cyclosporin A. Int J Pharm. 15; 274 (1-2):185-90).

The route of administration can be varied during a course of treatment.

Variables such as dosage amounts, and the mode, timing or frequency and duration of administration will vary depending on several factors including the age, weight and overall health of the patient as well as the state of the disease. These variables such as dosage amount may be determined in accordance with standard procedures in the art. In vitro experiments have shown that concentrations of the peptide of about 50 to about 100 micromolar were bacteriocidal to $10^5$ CFU per ml. Dosing may be daily (in one or more doses) for a total of 10 days or until no viable bacteria can be isolated from the patient's serum.

The invention will be further described by reference to the detailed examples. These examples are provided for purposes of illustration only, and are not intended to be limiting unless otherwise specified.

EXAMPLES

SRBC Lytic Assay

Various dilutions of the peptide were incubated with fixed amounts of sheep red blood cells in serum or in fibrin-free serum in a suitable assay plate. The plate was incubated for a period between 2 and 12 hours and the lytic activity was observed and recorded. Lysed red blood cells appeared as clear fluid in wells whereas unlysed cells maintained red color as RBCs remained intact.

Timekill Assays:

For *E. coli* time kill assays, cultures were inoculated 1:10 for 90 minutes, then the starter culture was diluted 1:50 and incubated for 90 minutes. The peptide and control were added at this juncture (t=0). *Bacillus anthracis* Sterne and *Bacillus subtilis* were grown in BS media (BSM) (1 L LB+5 g Nutrient Broth+1 mL 1M NaOH). In *Bacillus* time kill assays, approximately $10^5$ CFU of the test organism at mid-log phase was used to inoculate 2 mLs BSM and PAD 1.17 and controls added. Total viable bacterial counts (colony forming units, CFU) were determined by serial 10-fold dilution of culture aliquots in sterile medium, followed by spread plating of 100 mL samples of each dilution on LB agar plates in the absence of added antibiotics and overnight incubation at 37° C.

Germination Assay:

Spores were prepared by diluting confluent cultures of *Bacillus subtilis* or *Bacillus anthracis* Sterne 1:25 into Schaeffer's Sporulation Media. After 3 days of incubation at 37° C., cultures were determined to be >95% spores by phase-contrast microscopy. Spores were harvested via centrifugation, washed several times, and stored in sterile water. Prior to use in the germination assay, spores were activated by heating at 65° C. for 30 minutes. In germination assays, approximately $10^5$ spores were used to inoculate 2 mLs of BSM, with or without PAD-1.17. At time 0 and varying timepoints, aliquots were removed, serially diluted, and plated to determine CFU.

Results and Discussion

Figure 1B:
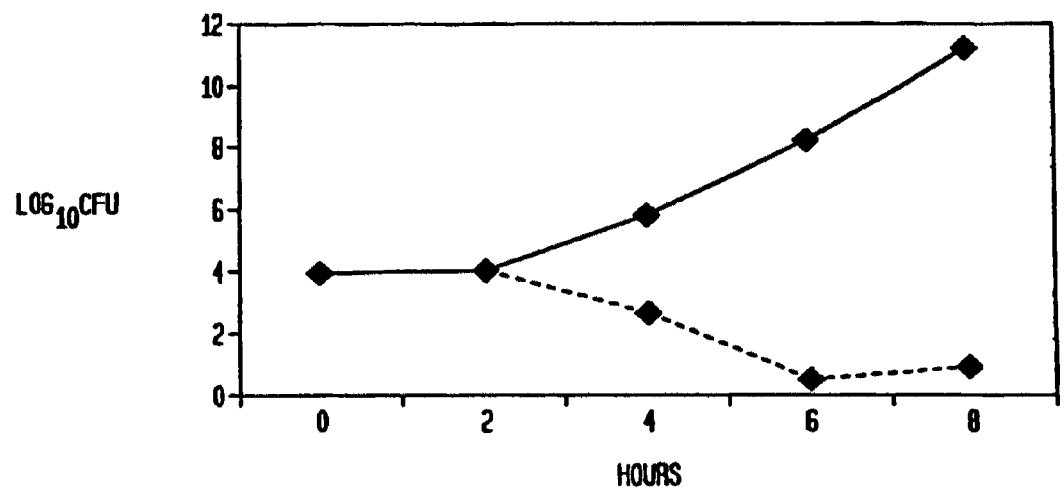
FIG. 1B is a line graph depicting the time kill assay of *E. coli* DC2 in the presence (dashed line) or absence (solid line) of PAD-1.17.
Figure 3:
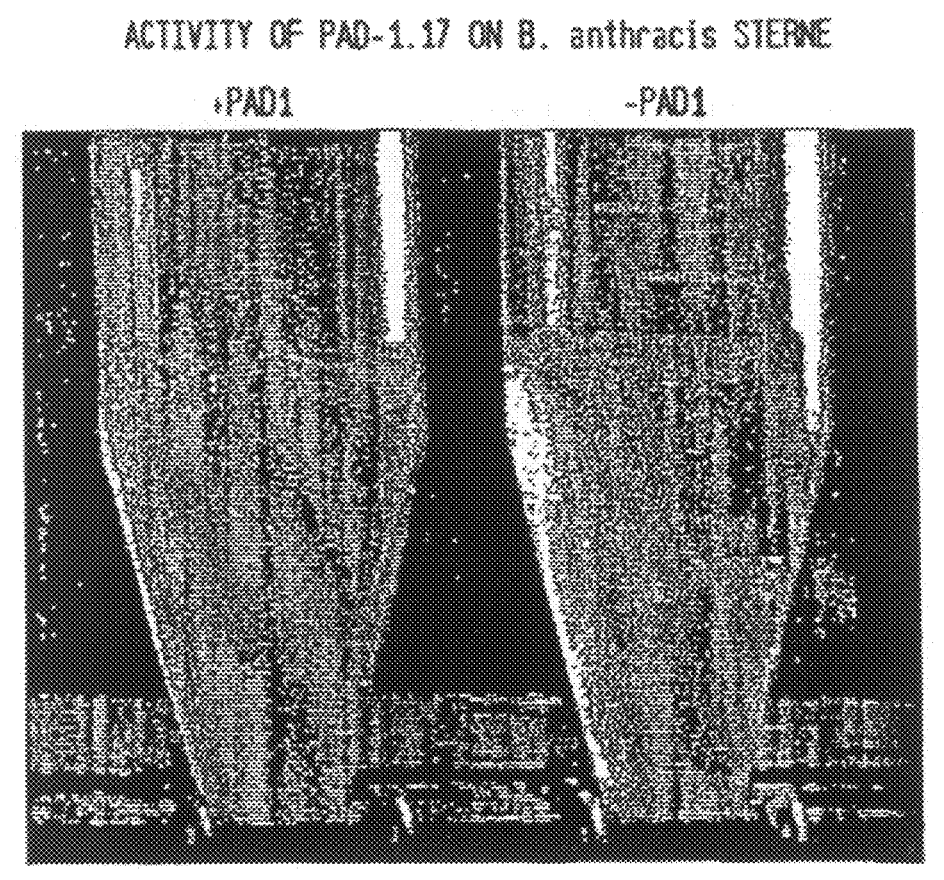

PAD-1.17 exhibited bacteriocidal effects against *E. coli* as a function of uptake. In the DH5α strain of *E. coli*, PAD-1.17 had a bacteriostatic effect over an 8 hour time period. (FIG. 1A.) However, in the DC2 strain of *E. coli*, which readily takes up foreign compounds, PAD-1.17 was bacteriocidal (FIG. 1B). In the two bacillus species examined, 100 μM PAD-1.17 killed an inoculum of $10^5$ *Bacillus anthracis* Sterne, and 50 μM PAD-1.17 killed an inoculum of $10^5$ *Bacillus subtilis* (FIGS. 2A and 2B). Protein kinase C, which has a size and pI similar to PAD-1.17, had no effect, indicating that the antibacterial activity of PAD-1.17 is specific. The bacteriocidal effect was apparent by six hours; tubes containing PAD-1.17 contained no visible growth (FIG. 3). In the germination assay, 50 μM PAD-1.17 prevented viable cells from emerging from an inoculum of $10^5$ spores from both species, as determined by calculating CFU from samples taken over a six-hour period (FIGS. 4A and 4B).

In addition to killing vegetative cells, PAD-1.17 also prevented the emergence of viable bacteria from bacillus spores. PAD-1.17 did not appear to act as a detergent, and a control peptide did not exhibit any antibacterial effects.

All publications cited in the specification including websites, are indicative of the level of skill of those skilled in the art to which this invention pertains. All these publications are herein incorporated by reference to the same extent as if each individual publication were specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An isolated peptide comprising the sequence TRKKLFHIFHATIRSR (PAD-1.17) (SEQ ID NO: 1).

2. A composition comprising a peptide comprising the sequence TRKKLFHIFHATIRSR (PAD-I.17) (SEQ ID NO: 1), and a carrier.

3. The composition of claim 2, wherein the carrier comprises phosphate buffered saline.

4. A method of treating an infection caused by spore-forming Gram-positive bacteria, comprising administering to a human in need thereof an effective amount of a peptide comprising the sequence TRKKLFHIFHATIRSR (PAD-1.17) (SEQ ID NO: 1).

5. The method of claim 4, wherein the infection is caused by a species of *Bacillus*.

6. The method of claim 5, wherein the infection is caused by *Bacillus cereus*.

7. The method of claim 6, wherein the infection is caused by *Bacillus anthracis*.

8. The method of claim 7, wherein the human is presenting with cutaneous anthrax.

9. The method of claim 7, wherein the human is presenting with pulmonary anthrax.

10. The method of claim 4, wherein the peptide is administered topically.

11. The method of claim 4, wherein the peptide is administered intravenously.

12. The method of claim 4, wherein the peptide is administered iontophoretically.

* * * * *

UNITED STATES PATENT AND TRADEMARK OFFICE
CERTIFICATE OF CORRECTION

PATENT NO.        : 8,227,423 B2                          Page 1 of 1
APPLICATION NO.   : 11/662555
DATED             : July 24, 2012
INVENTOR(S)       : Murphy It is certified that error appears in the above-identified patent and that said Letters Patent is hereby corrected as shown below:

In the Specifications

Column 1, line 56, "a" should read -- an --.

Column 5, line 32, "(PAD-I.17)" should read -- (PAD-1.17) --.

Signed and Sealed this
Seventh Day of January, 2014

Margaret A. Focarino
*Commissioner for Patents of the United States Patent and Trademark Office*

```
                              SEQUENCE LISTING

<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 1

Thr Arg Lys Lys Leu Phe His Ile Phe His Ala Thr Ile Arg Ser Arg
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 2

Arg Phe Ala Arg Lys Gly Ala Leu Arg Gln Lys Asn Val
1               5                   10
```